(12) United States Patent
Clark et al.

(10) Patent No.: US 6,938,503 B2
(45) Date of Patent: Sep. 6, 2005

(54) LYSIMETER APPARATUS

(75) Inventors: Don T. Clark, Idaho Falls, ID (US); Eugene E. Erickson, Pocatello, ID (US); William L. Casper, Rigby, ID (US); David M. Everett, Shelley, ID (US); Joel M. Hubbell, Idaho Falls, ID (US); James B. Sisson, Idaho Falls, ID (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 0 days.

(21) Appl. No.: 10/973,710

(22) Filed: Oct. 25, 2004

(65) Prior Publication Data

US 2005/0081654 A1 Apr. 21, 2005

Related U.S. Application Data

(62) Division of application No. 10/285,798, filed on Oct. 31, 2002, now Pat. No. 6,826,972.

(51) Int. Cl.[7] ............................................. E21B 43/00
(52) U.S. Cl. ................................ 73/863.23; 73/864.74; 175/60
(58) Field of Search ......................... 73/863.23, 863.24, 73/863.25, 864.74, 152.18, 866.5; 175/58–60

(56) References Cited

U.S. PATENT DOCUMENTS

| | | |
|---|---|---|
| 4,669,554 A | 6/1987 | Cordry |
| 4,807,707 A | 2/1989 | Handley et al. |
| 5,046,568 A | 9/1991 | Cordry |
| 5,337,838 A | 8/1994 | Sorensen |
| 5,465,628 A | 11/1995 | Timmons |
| 5,503,031 A | 4/1996 | Scott et al. |
| 5,889,217 A | 3/1999 | Rossabi et al. |

OTHER PUBLICATIONS

Karklins et al., "Groundwater Sampling Desk Reference", PUBL–DG–037 96, Wisconsin Dept. of Natural Resources Bureau of Drinking Water and Groundwater, Sep. 1996, pp. 88–89.*
Brye et al., "An Equilibrium Tension Lysimeter for Measuring Drainage through Soil", Journal of the Soil Science Society of America, 63:536–543, 1999.*
Wisconsin Dept. of Natural Resources, Groundwater Sampling Desk Reference, PUBL–DG–037 96, Sep. 1996.
Roger Davis and Tom Oothoudt, "Drilling method may be gold at end of rainbow for difficult terrains—option exists for drilling and collecting samples on one rig", Soil & Groundwater Cleanup, May 1997, pp. 34–36.

* cited by examiner

Primary Examiner—Charles Garber
(74) Attorney, Agent, or Firm—Wells St. John P.S.

(57) ABSTRACT

A suction lysimeter for sampling subsurface liquids includes a lysimeter casing having a drive portion, a reservoir portion, and a tip portion, the tip portion including a membrane through which subsurface liquids may be sampled; a fluid conduit coupled in fluid flowing relation relative to the membrane, and which in operation facilitates the delivery of the sampled subsurface liquids from the membrane to the reservoir portion; and a plurality of tubes coupled in fluid flowing relation relative to the reservoir portion, the tubes in operation facilitating delivery of the sampled subsurface liquids from the reservoir portion for testing. A method of sampling subsurface liquids comprises using this lysimeter.

8 Claims, 3 Drawing Sheets

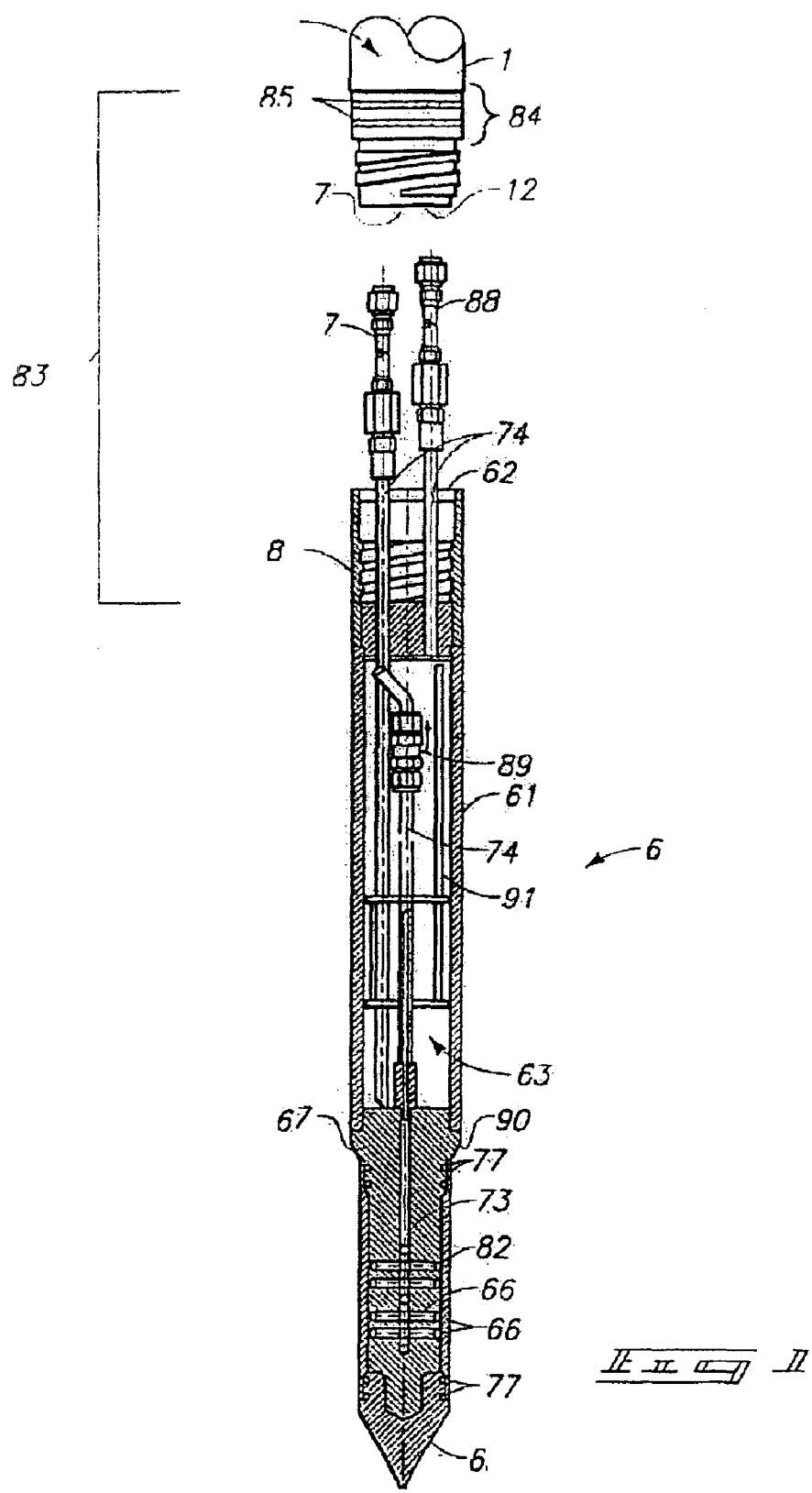

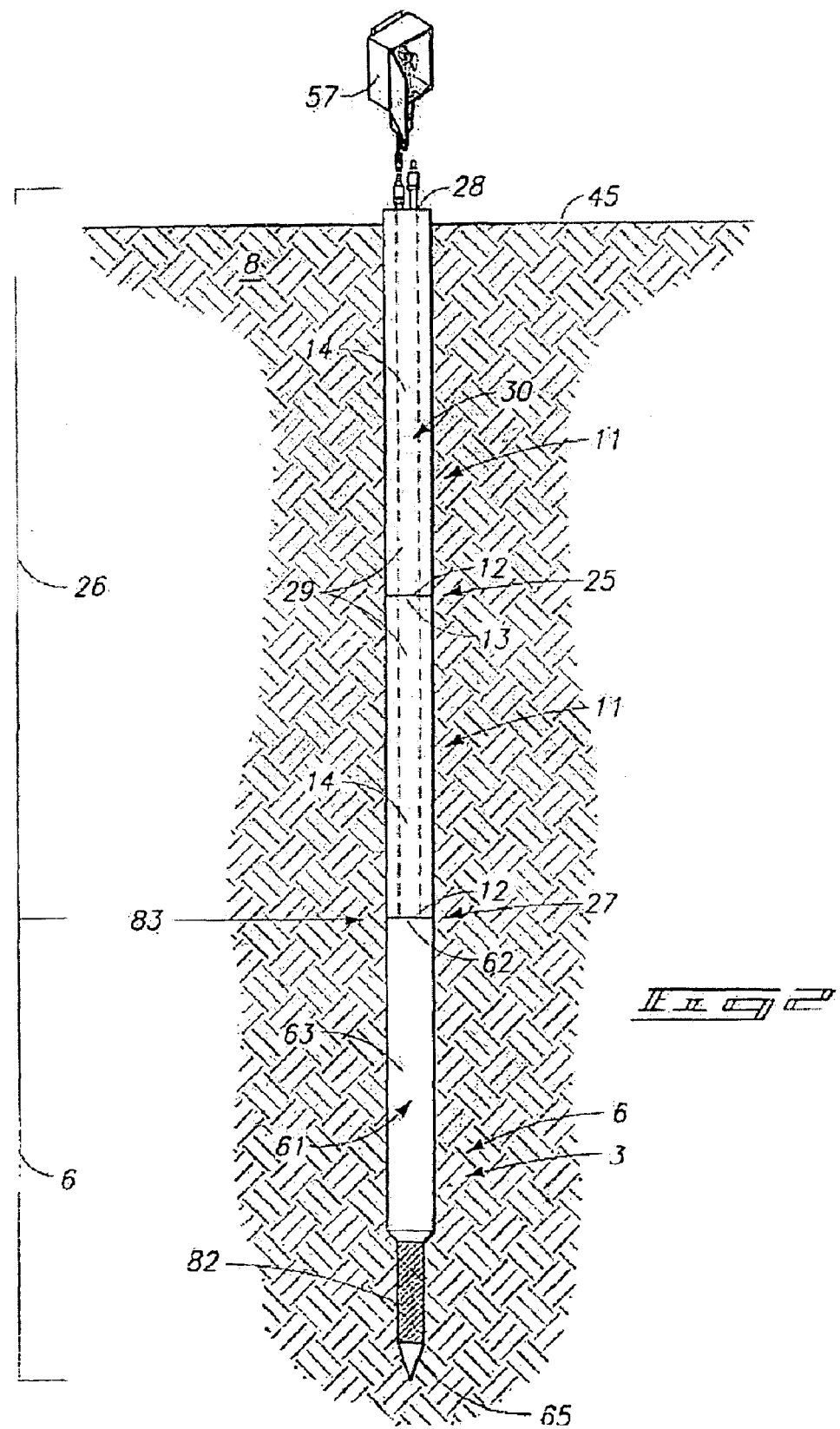

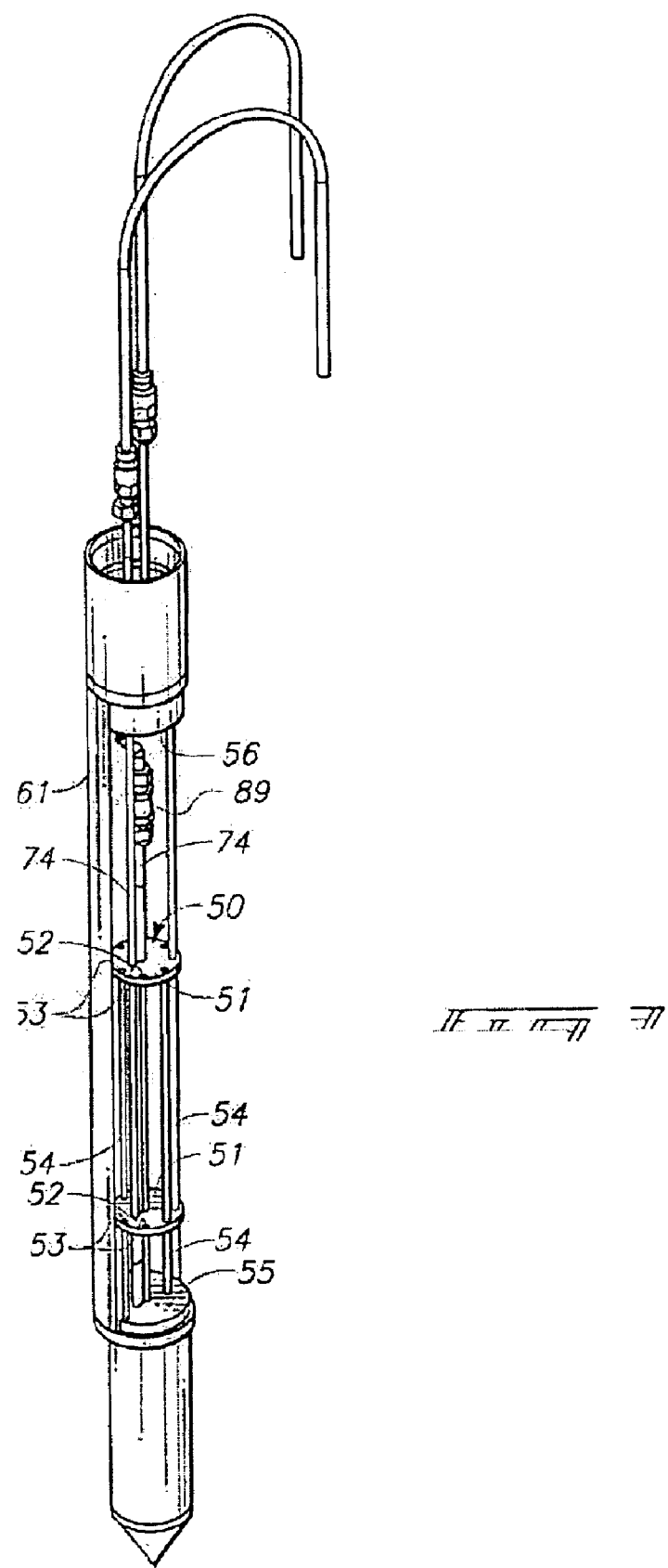

LYSIMETER APPARATUS

RELATENT APPLICATIONS

This application is a divisional of U.S. application Ser. No. 10/285,798, filed on Oct. 31, 2002 U.S. Pat. No. 6,826,972.

GOVERNMENT RIGHTS

This invention was made with Government support under Contract DE-AC07-99ID13727 awarded by the U.S. Department of Energy. The Government has certain rights in the invention.

TECHNICAL FIELD

The invention relates to methods and apparatus for subsurface testing. More specifically the invention relates to methods and apparatus for sampling subsurface liquids.

BACKGROUND OF THE INVENTION

Water and associated contaminants seep into the ground and travel through a subsurface region known as the vadose zone (a region of unsaturated soil). How the water and associated contaminants move in the vadose zone, to a large degree, determines how much contamination (such as gasoline additives, agricultural chemicals, or buried waste leakage) may end up in a water supply (such as an aquifer). Therefore, gaining an understanding of how the water and associated contaminants move in the vadose zone is valuable for appropriate waste containment. Information regarding the movement of water and associated contaminants in the vadose zone is generally acquired through the use of subsurface probes or similar testing devices. Several apparatus and methods have been used to facilitate such testing and information gathering. Some of these apparatus and methods involve obtaining samples of subsurface liquids, while others test soil moisture or other parameters.

In regard to sampling subsurface liquids, various methods and apparatus have been employed, including extraction of a soil core, introduction of vacuum-based or absorptive devices or materials, use of suction lysimeters, solution samplers, and other methods. Although there are several types of lysimeters, the term "lysimeter," will be used in this document to refer to a suction lysimeter.

The suction lysimeter is a hydrological instrument used to sample liquids or to monitor soil or like substrates. The lysimeter accomplishes this function by application of vacuum or pressure gradient principles such that the liquid of interest is drawn toward the lysimeter permitting collection of a liquid sample. Although the lysimeter is primarily a sampling device, it may also be used to provide an indication of the water pressure (positive or negative). This is done by applying a vacuum, allowing the sampler to pressure equilibrate with the surrounding material being sampled, and recording this pressure.

Although prior lysimeters have been useful in gathering much information, such lysimeters have several shortcomings which have limited their usefulness. For example, prior lysimeters cannot be installed without prior excavation or drilling, and in contaminated areas such excavation or drilling is highly undesirable as it would tend to spread contamination. Additionally, such lysimeters have provided only small samples of subsurface liquids.

Another problem is that lysimeters are very fragile. They are made of ceramic, tin, copper, plastics, or similar such materials and cannot be installed directly through difficult materials such as hardened soils, concrete, steel, other metals, or waste products.

Monitoring and testing to determine the movement of subsurface water and associated contaminants is particularly valuable when dealing with waste disposal sites that contain radiological contaminants or other hazards. However, as described above, placing probes into the subsurface for data collection in such sites has not been feasible, because the placing of such probes would require drilling or coring which would bring contaminated "cuttings" to the surface and would create a pathway through which contaminated emissions may escape. As a result, test probes have typically been placed in areas around such waste sites. Unfortunately, such probe placement only provides information when the contaminants have already migrated outside of the waste disposal site area. Moreover, at the point when the contaminants have already migrated outside of the waste disposal site area, it is likely that a major contaminant plume already exists in the subsurface soil and aquifer making remediation and containment efforts much more difficult and costly.

In view of the foregoing, it would be highly desirable to provide methods and apparatus which facilitate subsurface testing and sampling in both contaminated and non-contaminated areas, while substantially avoiding these and other shortcomings of the prior devices.

BRIEF DESCRIPTION OF THE DRAWINGS

Preferred embodiments of the invention are described below with reference to the following accompanying drawings.

FIG. 1 is a front elevational view, partly in section, showing a lysimeter in accordance with one embodiment of the present invention, and also showing a portion of a probe casing.

FIG. 2 is a front elevational view, partly in section, showing probe casings and the lysimeter of FIG. 1 positioned for use in a substrate. The lysimeter cap is also shown.

FIG. 3 is a perspective view, partly in section, showing a lysimeter in accordance with one embodiment of the present invention.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

The invention relates to methods and apparatus for subsurface testing. More specifically, the invention relates to methods and apparatus for sampling subsurface liquids from the substrate. One embodiment of the invention allows such sampling to be carried out in either contaminated or non-contaminated sites without the need for drilling, coring, or prior excavation. In one embodiment, a method includes placing the instrumented probe into the substrate using direct push, sonic drilling, or a combination of direct push and sonic drilling.

FIGS. 1 and 2 show a lysimeter 6 for sampling subsurface liquids. The lysimeter 6 includes a lysimeter casing 61. The lysimeter casing 61 includes a drive portion 62, a reservoir portion 63, and a tip portion 65. The tip portion 65 includes a sample passageway 66, through which subsurface liquids may be sampled. A fluid conduit 73 is coupled in fluid flowing relation relative to the sample passageway 66, and in operation facilitates the delivery of the sampled subsurface liquids from the sample passageway 66 to the reservoir portion 63 of the lysimeter 6. A plurality of tubes 74 are provided. One of the tubes is a sampling tube that facilitates delivery of the sampled subsurface liquids from the reservoir portion 63 to the land's surface 45 for testing. Another of the tubes 74 is used for applying a vacuum or pressure.

In one embodiment, the sample passageway 66 for sampling subsurface liquids comprises nominal pore openings of about 0.2 micron to about 1 micron through a stainless steel membrane 82; however, other materials and sizes are possible. The stainless steel membrane 82 may be affixed in any appropriate manner. For example, in one embodiment the stainless steel membrane 82 may be welded into place. In the depicted embodiment the stainless steel membrane 82 is held captive by the tip 65. The tip 65 and nose portion 67 shield the stainless steel membrane 82 from large compressive and tensile loads. The nose portion 67 is longer than the membrane 82 and therefore picks up compressive and tensile loading that could otherwise be seen by the membrane 82. O-rings 77 provide a seal. The reservoir portion 63 of the lysimeter 6 has, in one embodiment, a volume of about one liter. However, other volumes are contemplated.

A step 90 provides a compacting function and provides for good contact with the soil. The step is achieved by an increase in diameter or periphery relative to length.

FIG. 3 shows construction details of a tube spacer assembly or impact delimiter 50. The spacer 50 absorbs vibration and holds the reservoir sample tubes 74 in place. The spacer 50 is constructed from two thin circular plates or disks 51 that have holes in them. The larger holes 52 are openings for the tubes 74 to pass through. The plates 51 also have smaller holes 53 (which are located proximate the plate's perimeter in the illustrated embodiment) that allow the sample to pass through them. The two plates 51 are connected together by rods 54. In one embodiment, the rods 54 are weld filler rods that are fused to the two disks. In alternative embodiments, the rods are thin rods constructed from wire, thin bar shapes, etc. Using weld filler rod provides for a simple construction. The tube spacer assembly's purpose is to protect the lysimeter components within the upper reservoir 63 from the vibrational loads they would normally experience while the probe is being advanced into the ground. The tube spacer assembly 50 acts as a impact delimiter to absorb vibrational energy and minimize tube 74 lateral deflection. The reservoir tubes 74 will deflect, but the spacer assembly 50 prevents large displacements, which in turn protects tube connection welds, and therefore protects the internal components from shaking themselves apart. The tube spacer assembly 50 is built for flexibility and is a sacrificial component (i.e., is allowed to impact the reservoir's internal cavity walls and deform) so that the internal tube and connection components are not damaged. If the tube spacer assembly 50 is not used, it is possible that the internal reservoir tubing 74 and valve 89 would oscillate within the reservoir 63 during sonic probe advancement, and become bent, damaged, and compromise the lysimeter's function.

The tube spacer assembly 50 utilizes the circular plates (or disks) to absorb energy from lateral vibrational loads. The disks 51 impact the internal reservoir walls and are allowed to plastically deform (i.e., bend), but also prevent the tube components 74 and valve 89 from swinging or experiencing large deflections. The two disks are used along the internal tubing length, to provide uniform displacement control. The extending rods 54 connect the disks 51 together and also are extended within the reservoir to the cavity ends 55 and 56, so that the disks 51 remain in approximately the same position along the reservoir's length. In the illustrated embodiment, the tube spacer assembly 50 is constructed entirely from stainless steel, for maximum corrosion resistance. The weld filler rod is also constructed from stainless steel. In this way, the water sample is not contaminated by the tube spacer within the reservoir 63. The tube spacer assembly 50 could be constructed from other materials as well.

The lysimeter casing 61 shown in FIGS. 1–3 comprises stainless steel. However, any suitable material may be used to construct the lysimeter casing or tubing 61. In one embodiment, the lysimeter casing 61 comprises stainless steel, and is of adequate durability for installation into a substrate by direct push, by sonic drilling, or by a combination of direct push and sonic drilling.

Referring again to FIGS. 1 and 2, the drive portion 62 of the lysimeter casing 61 is configured to selectively couple to the end 12 of a probe casing 11 at a drive connection joint 83 (only a portion of a probe casing 11 is shown in FIG. 1). Stated in other terms, the drive portion 62 of the lysimeter casing 61 is configured to selectively couple to the instrument receiving end 27 of an insertion tube 26 at the drive connection joint 83. The drive connection joint 83 includes a drive connection seal 84 which functions as a substantial barrier to contaminants.

As shown in FIG. 1, in one embodiment, the drive connection seal 84 comprises a plurality of seals. Specifically, in the depicted embodiment, the drive connection seal 84 comprises two seals, such as two o-ring seals 85, which function as a substantial barrier to contaminants. The drive connection joint 83 includes a bearing surface 86 which functions to isolate the drive connection seal 84 and to protect the drive connection seal 84 from large loads as the lysimeter 6 is inserted into the ground 8.

Referring to FIG. 2, a plurality of probe casings 11 are shown coupled in series to form an insertion tube 26 (i.e. two such probe casings 11 are shown). The insertion tube 26 has an instrument receiving end 27 which is configured to selectively couple with the drive portion 62 of the lysimeter casing 61. The insertion tube 26 also has a surface end 28 and an insertion tube wall 29. Together, the instrument receiving end 27, the surface end 28, and the insertion tube wall 29 define a central cavity 30 (shown in phantom lines). A lysimeter cap 57 is configured for ground surface connection and prevents incorrect vacuum pump attachment. The cap 57 is also weather resistant, lending further protection to instruments above ground surface As described above, the plurality of probe casings 11 are selectively coupled to form an insertion tube 26. In the illustrated embodiment, the insertion tube 26 so formed has an outside diameter or periphery of less than four inches. The outer wall or sidewall 14 of the probe casings 11 defines an outside diameter or periphery of the probe casings, which is the same as the outside diameter or periphery of the insertion tube 26 formed when the respective probe casings 11 are selectively coupled (FIG. 2). In one embodiment, the outside diameter of the insertion tube 26 is less than five and five-eighths inches. In one embodiment, the outside diameter of the insertion tube 26 is about two and one-half inches. Other sizes are possible. In one embodiment, the lysimeter casing 61 has an outside diameter or periphery corresponding to the outside diameter or periphery of the probe casings. For example, in one embodiment, the outside diameter of the lysimeter casing 61 is less than five and five-eighths inches. In one embodiment, the outside diameter of the lysimeter casing 61 is about two and one-half inches.

As shown in FIG. 1, the instrument receiving end 27 of the insertion tube 26 and the drive portion 62 to the lysimeter casing 61 are configured so that they may be easily coupled. In one embodiment, selectively coupling the instrument receiving end 27 of the insertion tube 26 to the drive portion 62 to the lysimeter casing 61 requires less than four turns to fully engage the drive connection joint 83 and drive connection seal 84. In the depicted embodiment, selectively coupling the instrument receiving end 27 of the insertion tube 26 to the drive portion 62 to the lysimeter casing 61 requires two and one-half turns to fully engage the drive connection joint 83 and drive connection seal 84.

As shown in FIGS. 1 and 2, the insertion tube 26 functions as a conduit through which the plurality of tubes 74 may pass. In operation, one of the tubes 74 can be used to transfer sampled subsurface liquids to the land's surface 45.

The insertion tube 26 and the lysimeter casing 61 are of an adequate durability for installation into the ground 8 by direct push, by sonic drilling, or by a combination of direct push and sonic drilling.

FIGS. 1–3 also depict methods of sampling subsurface liquids. One method includes providing a lysimeter probe 6. The lysimeter probe 6 provided has a lysimeter casing 61 comprising or defined of (in one embodiment) stainless steel. The lysimeter casing 61 includes a drive portion 62, a reservoir portion 63, and a tip portion 65. The tip portion 65 includes a sample passageway 66. An insertion tube 26 is also provided. This insertion tube 26 includes a plurality of probe casings 11 which have been selectively coupled at casing joints 25.

The insertion tube 26 formed by the selectively coupled probe casings 11 has an instrument receiving end 27, a surface end 28, and an insertion tube wall 29 which together define a center cavity 30. The instrument receiving end 27 of the insertion tube 26 and the drive portion 62 of the lysimeter casing 61 are selectively coupled at a drive connection joint 83. The drive connection joint 83 includes a drive connection seal 84 which functions as a substantial barrier to contaminants. A fluid conduit 73 which is coupled in fluid flowing relation relative to the sample passageway 66 is provided. In operation, the fluid conduit 73 facilitates the delivery of sampled subsurface liquids from the sample passageway 66 to the reservoir portion 63. The sampling tubes 74 are coupled in fluid flowing relation relative to the reservoir portion 63, and extend through the center cavity 30 of the insertion tube 26, to facilitate delivery of the sampled subsurface liquids from the reservoir portion 63 to the land's surface 45 for testing. The tubes typically include at least one vacuum tube 88 and one sample tube 87.

The insertion tube 26 and selectively coupled lysimeter 6 are placed into the ground 8 by direct push, by sonic drilling, or by a combination of direct push and sonic drilling. According to one method, the lysimeter 6 is placed into the ground 8 to a desired depth. One method includes driving the lysimeter 6 into the ground 8 so that the membrane 82 will be in contact with subsurface liquids. Vacuum pressure is then provided to the vacuum tube 88 to pull a sample of the subsurface liquids into the reservoir portion 63 of the lysimeter 6. Air pressure is provided to the air tube 88 to push the sample of subsurface liquids elevationally upwards through the sample tube 87. The air pressure closes a check valve 89 to prevent a sample from being blown out through the sample passageway 66. The check valve 89 is omitted in alternative embodiments, such as in deep installations.

A lysimeter has been disclosed that, in one embodiment, is of all stainless steel construction for corrosion resistance and longevity, with a porous stainless steel membrane design. The tip design isolates and protects the porous membrane from large tension and compression loads during probe installation. The design allows for easy replacement of or size selection for the porous membrane (as required). A robust design has been disclosed for large load (i.e., direct push, sonic, or a combination) emplacement through difficult materials (such as hardened soils, concrete, steel, other metals, etc.) The entire lysimeter is put in place with one action (there are not multiple parts), in one embodiment. A double (redundant) o-ring design impedes contamination transfer. An inner spacer component protects sampling instrumentation from excessive vibrations. The lysimeter is designed for ground retraction, instrument and/or tip replacement, and reuse. A lysimeter cap is configured for ground surface connection and prevents incorrect vacuum pump attachment. The cap is also weather resistant, lending further protection to instruments above ground surface.

The invention provides robust lysimeters that are particularly useful for driving into highly contaminated waste, as well as other uses. The lysimeters can be driven into difficult materials (e.g., hardened soils, concrete, steel, other metals, etc.) that would typically damage other tools. In the illustrated embodiments, small diameter designs are employed that require less energy for installation into a sample. Reduced energy requirements allow for smaller driving equipment resulting in lower cost.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A suction lysimeter for sampling subsurface liquids, comprising:

a lysimeter casing having a drive portion, a reservoir portion, and a tip portion, the tip portion including a porous stainless steel membrane through which subsurface liquids may be sampled, the porous stainless steel membrane having pore openings no greater than 1 micron in size, the tip portion further including a tip member, and a nose portion having an outer cylindrical surface, and having an enlarged diameter portion defining an abutment surface, the membrane having an inner cylindrical surface slidingly received on the outer cylindrical nose portion, the membrane having a first end that abuts the abutment surface and having a second end, the tip member being directly secured to the nose portion and including an abutment surface that abuts the second end of the membrane, such that the membrane is held floating between the tip member and the enlarged diameter portion of the nose portion, the membrane having a length, and the nose portion having a length longer than the length of the membrane, wherein loads applied to the tip member are substantially transferred to the nose portion but not to the membrane;

a fluid conduit coupled in fluid flowing relation relative to the membrane, and which in operation facilitates the delivery of the sampled subsurface liquids from the membrane to the reservoir portion; and a plurality of tubes coupled in fluid flowing relation relative to the reservoir portion, the tubes in operation facilitating delivery of the sampled subsurface liquids from the reservoir portion for testing.

2. The suction lysimeter of claim 1, and further comprising a seal between the tip member and the membrane.

3. The suction lysimeter of claim 2 wherein the seal comprises a plurality of seals.

4. The suction lysimeter of claim 3, wherein the seal comprises two seals that function as a substantial barrier to contaminants.

5. The suction lysimeter of claim 1 wherein the tip portion and nose member include peripheral o-rings, and wherein the membrane has one end sealingly engaging the o-ring of the tip portion and another end sealingly engaging the o-ring of the nose member, and wherein the tip floats on the o-rings, wherein the tip portion and nose member shield the membrane from compressive, tensile, bending, and penetration loads.

6. The apparatus of claim 5, wherein the nose portion has a length, wherein the membrane has a length, and wherein the length of the nose portion is longer than the length of the membrane.

7. The apparatus of claim 1 and further comprising an impact delimiter in the housing, the impact delimiter including first and second spaced apart plates that have apertures therethrough which the tubes pass through, the first and second plates being connected together by spaced apart rods, whereby the impact delimiter is configured to protect at least the tubes from vibrational loads.

8. The apparatus of claim 1 wherein the tip member is removably attached to the nose portion, wherein the membrane can be removed and replaced, by removing the tip member from the nose portion, sliding off the membrane, sliding on a replacement membrane, and reattaching the tip member to the nose portion.

* * * * *